(12) United States Patent
Frische et al.

(10) Patent No.: US 6,527,707 B1
(45) Date of Patent: Mar. 4, 2003

(54) ENDOSCOPE WITH A WORKING PASSAGE

(75) Inventors: Holger Frische, Buchholz (DE);
Frank-Michael Smid, Hamburg (DE);
Uwe Schrader, Hamburg (DE)

(73) Assignee: Olympus Winter & IBE GmbH, Hamburg (DE)

( * ) Notice: Subject to any disclaimer, the term of this patent is extended or adjusted under 35 U.S.C. 154(b) by 235 days.

(21) Appl. No.: 09/596,735

(22) Filed: Jun. 19, 2000

(30) Foreign Application Priority Data

Jun. 22, 1999 (DE) .......................................... 199 28 289

(51) Int. Cl.[7] ................................................ A61B 1/00
(52) U.S. Cl. ...................................... 600/153; 600/156
(58) Field of Search .............................. 600/153, 154, 600/156, 159, 158

(56) References Cited

U.S. PATENT DOCUMENTS

| | | | | |
|---|---|---|---|---|
| 3,782,369 A | * | 1/1974 | Storz | 600/156 |
| 3,850,175 A | * | 11/1974 | Iglesias | 600/105 |
| 4,653,475 A | * | 3/1987 | Seike et al. | 600/104 |
| 4,706,656 A | * | 11/1987 | Kuboto | 600/153 |
| 5,048,508 A | * | 9/1991 | Storz | 600/116 |
| 5,287,845 A | * | 2/1994 | Faul et al. | 600/135 |
| 5,301,656 A | * | 4/1994 | Negoro et al. | 600/133 |
| 5,575,756 A | * | 11/1996 | Karasawa et al. | 600/121 |
| 5,888,191 A | * | 3/1999 | Akiba et al. | 600/153 |
| 5,891,014 A | * | 4/1999 | Akiba | 600/156 |
| 5,971,917 A | * | 10/1999 | Komi et al. | 600/154 |
| 6,358,200 B1 | * | 3/2002 | Grossi | 600/121 |

* cited by examiner

*Primary Examiner*—Linda C. M. Dvorak
*Assistant Examiner*—Jocelyn Ram
(74) *Attorney, Agent, or Firm*—Rankin, Hill, Porter & Clark LLP

(57) ABSTRACT

A medical endoscope with a sealed housing that defines a shaft. A working passage, which is open at its ends, extends through the shaft in a sealed manner in the longitudinal direction. The passage projects proximally beyond the housing and has a lateral branch passage for connection of a flow line. The branch passage is arranged on the housing so as to pass through the housing wall and a wall defining the working passage.

3 Claims, 1 Drawing Sheet

ENDOSCOPE WITH A WORKING PASSAGE

BACKGROUND OF THE INVENTION

The present invention generally relates to medical endoscopes having elongated shafts and sealed housings that define a working passage, the working passage having a lateral branch passage for connection to a flow line.

Endoscopes of this type, which is referred to as solid shaft type, are used, for instance, in laparoscopy or in the field of urology as a nephroscope and ureteroscope. The working passage, which passes through the entire length of the endoscope, is open at its ends and is used for introducing working instruments through the length of the endoscope to the operational region. The housing sealingly surrounding the working passage accommodates devices in its interior which are required for operation of the endoscope and which must be protected from moisture during operation of the endoscope and, particularly, steam and moisture during the subsequent sterilization of the endoscope. Such devices are, in particular, an optical system, an illumination device, for instance in the form of the conventional light guiding fiber bundle, or other e.g. electronic devices. A very good seal of the housing is of importance for a long-life construction of the endoscope.

The working passage in instruments of the type referred to above is also used as a flow conduit to communicate fluid to/from the operational region. For this purpose, a lateral branch passage is provided to which further flow lines may be connected. The proximal end of the working passage can be commonly closed with a valve and the branch passage can be commonly opened with a further valve in order to pump, for example, flushing liquid to the operational region through the distal portion of the branch passage or to draw fluid from the operational region. Gas, for instance, can also be exhausted or admitted through the flow line.

Such endoscopes can also have an additional outer shaft over the main shaft which is disposed around the distal insertion region of the main shaft and is removably coupled to it, for instance, with a coupling on the main body proximately adjoining the shaft. The space between the main shaft and outer shaft can be used as a flushing or suction passage, for which purpose a further branch passage is provided on the outer shaft connected to the space between the shafts.

In known endoscopes, the branch passage is connected to the portion of the working passage extending proximally beyond the housing. This type of connection offers the advantage of a simple construction but has the disadvantage that a hose hanging from the branch passage while working with the endoscope is situated too proximally. Therefore, the branch passage at this position loads the endoscope with its weight too far proximally behind the center of gravity of the device. Moreover, placing the branch passage at this location situates it in the proximal region, which is required by the operator for gripping purposes and for viewing at the ocular of the optical system.

In a different type of endoscope which is used as a urological resectoscope and which is disclosed in DE 41 01 472 C1, a shaft is provided with a rotationally coupled outer shaft. Two branch passages are provided on the outer shaft, of which one is connected to the space between the shafts and the other is connected via a sealed annular passage and an opening in the inner shaft to the latter. This device is designed in accordance with the hollow shaft principle and thus does not have the problem of a sealed housing in the vicinity of the branch passages.

SUMMARY OF THE INVENTION

It is the object of the present invention to construct an endoscope of the type referred to above such that the branch passage and associated hoses impair working with the endoscope to a lesser extent.

In accordance with the present invention, the branch passage is not provided directly on the working passage in its region projecting proximally beyond the housing but in the region of the housing and passing through it. Therefore, the branch passage is disposed substantially further distally, particularly distally of the outlets of the optical system and of the light guide. Hoses to be attached to the branch passage can be moved together with the other lines extending away, e.g. a light guide cable, into a favorably balanced position with respect to the center of gravity. The branch passage is also situated remote from the working region of the operator. Disruptions by the branch passage and hoses disposed thereon are substantially limited. One can work substantially more easily and simply with the endoscope in accordance with the invention.

In further accordance with the present invention, a sealing body surrounds the branch passage and is disposed between the working passage and the housing. As such, the necessary seal of the branch passage with respect to the interior of the housing can be effected in a constructionally simple manner.

The branch passage can be fixedly arranged on the housing. However, in further accordance with the present invention, an inner portion communicates with an inner peripheral passage in a ring that is disposed around the housing. Therefore, the branch passage is pivotable about the axis of the endoscope so that it can be set at a favorable angle in all rotary positions of the endoscope, for instance pointing downwardly.

BRIEF DESCRIPTION OF THE DRAWINGS

These and further features of the present invention will be apparent with reference to the following description and drawings, wherein.

DETAILED DESCRIPTION OF THE PREFERRED EMBODIMENT

Figure 1:
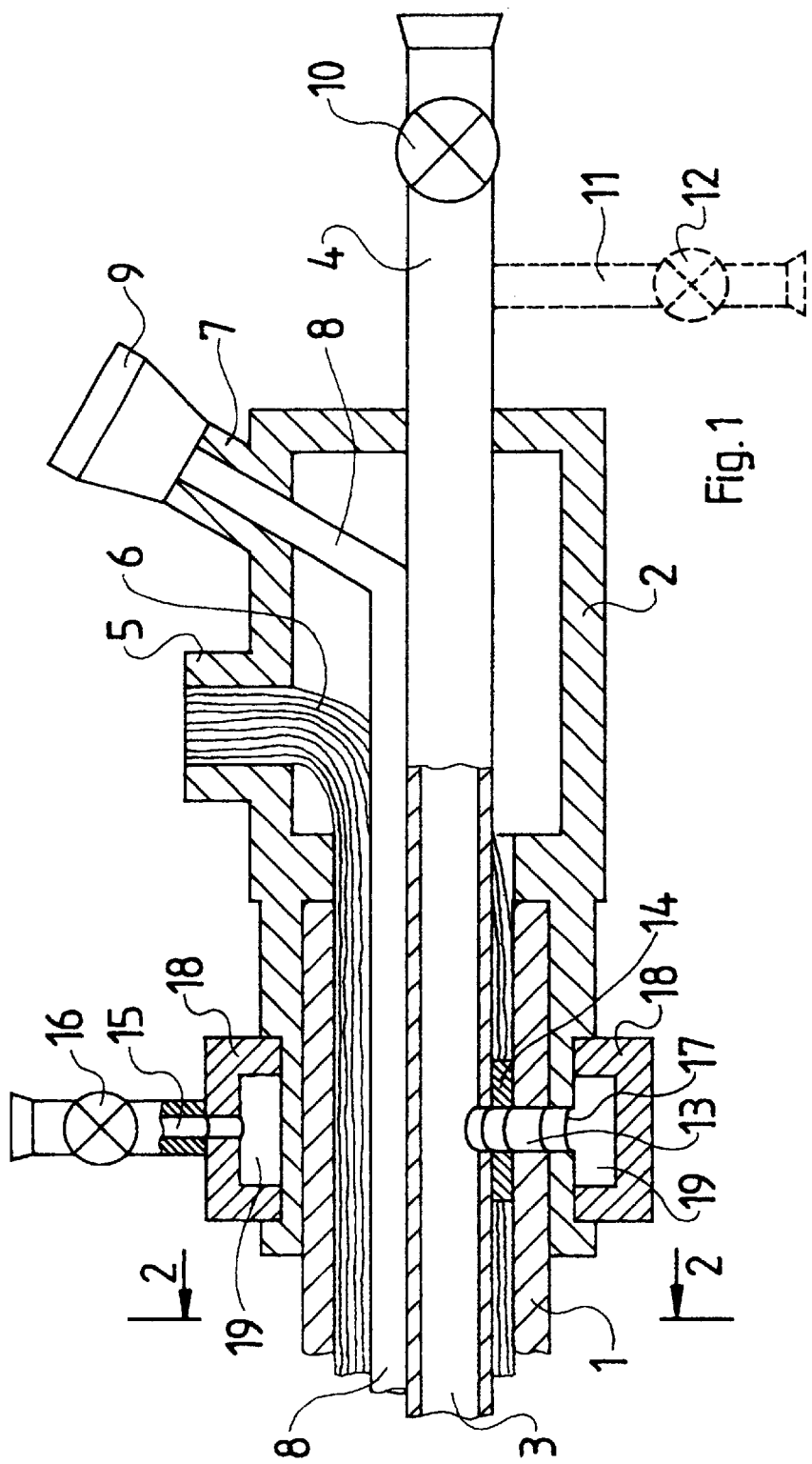
FIG. 1 is an axial sectional view of an endoscope according to the present invention.
Figure 2:
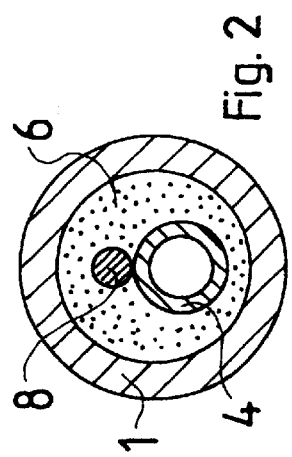
FIG. 2 is a sectional view of the endoscope as seen along the line 2—2 in FIG. 1.

As shown highly schematically in the figures, the endoscope has a housing which comprises a tubular shaft 1, which is to be introduced into the body of the patient, and a main body 2 adjoining the shaft 1. The main body 2 is secured to the proximal end of the shaft 1, and the shaft extends away from the main body 2. These two components are connected together, for instance by adhesive, soldering or the like, in a sealed manner which will not be described in more detail.

A working tube 4, which surrounds and defines a working passage 3, extends through the housing 1, 2. The tube 4 passes, in a sealed manner, through the end wall of the main body 2 in order to project beyond the main body 2 with a proximal end region. The tube 4 essentially extends from the main body 2 in a direction opposite to, and aligned with, the shaft 1.

Secured in a connecting socket 5 on the main body 2, which serves to connect a light guiding fiber cable, is the proximal end of a light guiding fiber bundle 6. The fiber bundle 6 extends through the interior of the housing 1, 2 in the longitudinal direction toward the distal end of the shaft 1. An ocular socket 7 also extends away from the main body 2. An optical system extends through the ocular socket 7 and through the shaft 1 to the distal end of the endoscope. An ocular 9 is provided at the proximal end of the optical system 8 on the ocular socket 7.

The housing 1, 2 is closed in a sealed manner at the distal end (not shown) of the shaft 1 in a suitable manner. For instance, the shaft may be sealed or closed by a window for the optical system 8 and with a sufficiently sealed adhesion of the fibers of the light guiding fiber bundle 6, which fill the area within the shaft 1 and outside the working tube 4 and the optical system 8. The well-sealed housing 1, 2 ensures that the optical system 8 disposed therein and the light guiding fiber bundle 6, which can be freely disposed therein, are not impaired by water or vapor which penetrates while working with the endoscope or during sterilization.

On the other hand, the working passage 3, provided by the tube, is open at both ends. Preferably, a proximal end of the passage tube 4 has a valve 10 with which the passage 3 may be blocked.

The endoscope described above is known from the prior art. Such known endoscopes have, at the end region of the working passage 3 projecting proximately beyond the housing 1, 2, a branch passage 11 with a valve 12 connected laterally to the working tube 4, as is illustrated in broken lines in FIG. 1 for the purpose of explanation. Connected to the branch passage 1, there can be a flow line which extends away in the form of a hose. After closing the valve 10 and opening the valve 12 the working passage 3 can be used for introducing or draining flushing liquids, gases and the like. As shown in FIG. 1, the hose extending away from the branch passage 11 is then, however, situated too far in the proximal direction, that is to say proximally of the ocular 9 and of a light guiding cable extending away from the connecting socket 5. The result of this is an unfavorable location of the center of gravity and an impairment of the working field of the operator by the hose.

The inventive construction illustrated in FIG. 1, on the other hand, provides an inner branch passage 13 that passes through the wall of the main body 2. The inner branch passage 13 surrounds the shaft 1 at that point, and the shaft 1 itself and the wall, of the working tube 4. Provided between the working tube 4 and the shaft 1 is a sealing body 14, which, constructed in a suitable shape, sealingly engages around the edge of the inner branch passage 13 between the wall of the working tube 4 and the shaft 1 and which is sealingly secured in a suitable manner, for instance by adhesive, soldering or the like. The sealing body 14 ensures a good seal of the inner branch passage 13 with respect to the interior of the housing 1, 2. It can also be constructed, for instance, in the form of a short tubular member extending transverse to the axis of the working tube 4.

An outer branch passage 15 with a valve 16 is secured directly to the outer opening 17 of the inner branch passage 13. In the event that the shaft 1 is not surrounded by the main body 2 at that point, the outer branch passage 15 should be secured directly to the shaft 1.

In the illustrated exemplary embodiment the outer branch passage 15 is, however, arranged to be pivotable about the axis of the shaft 1.

The outer branch passage 15 is secured to a ring or collar 19 that extends over the outer mouth 17 of the inner branch passage 13 with an inner peripheral passage 19. The ring 18 is, as shown, mounted rotatably on the main body 2, retained in the axial direction, and rotationally seated with means which are not shown. With this construction, a flow passage is ensured from the working passage 3 to a hose (not shown) connected to the outer branch passage 15 in all angular positions of the outer branch passage 15 about the axis of the shaft 1. The ring 18 may be removed from the main body 2 for cleaning purposes. The branch passage 15 can also be provided in a different axial position on the illustrated endoscope, for instance in the axial position of the connecting socket 5. It can be provided there, for instance, diametrically opposite thereto, whereby a rotatable construction with ring 18 is then not possible. Such a rotatable construction would, however, be possible on the main body 2 between the connecting socket 5 and the ocular socket 7.

An outer shaft surrounding the shaft 1 can be provided in the conventional manner. The outer shaft can be secured, for instance, to the ring 18 and proximately sealed to it. The additionally provided outer shaft can be rotatably mounted with the ring 18 and be constructed to be decoupled with it. A further branch passage with a valve can be provided on the additional outer shaft which results in a further hose connection to the space between the shaft 1 and the additional outer shaft.

What is claimed is:

1. A medical endoscope with a sealed housing (1, 2) that defines an elongated shaft (1) through which a working tube (4) extends, said working tube being sealed to the housing in a vapor-tight manner such that a working passage defined by said working tube is fluidly isolated from an interior of said shaft (1), said working tube being open at both ends and projecting proximally beyond the housing, said working passage being in fluid communication with a lateral branch passage (13, 15) for connecting a flow line, wherein the branch passage (13) passes through a wall of the housing (1, 2) and through a wall of the working tube (4).

2. The medical endoscope as claimed in claim 1, wherein a sealing body (14) is disposed between the walls of the working tube (4) and the housing (1, 2), said sealing body (14) surrounding the branch passage (13).

3. The medical endoscope as claimed in claim 1, wherein the branch passage includes an inner portion (13), which discharges to an exterior at the wall (1, 2) of the housing, and opens out into an inner peripheral passage (19) in a ring (18), said ring being rotatably mounted on the housing (2) in a sealed manner, an outer portion (15) of the branch passage extending away from said ring.

* * * * *